(12) United States Patent
Tan et al.

(10) Patent No.: US 11,357,843 B2
(45) Date of Patent: Jun. 14, 2022

(54) BACTERIOLOGICALLY-MODIFIED WHOLE-CELL TUMOR VACCINE AND METHOD OF MAKING SAME

(71) Applicant: Hainan Medical University, Hainan (CN)

(72) Inventors: Guang-Hong Tan, Haikou (CN); Feng-Ying Huang, Haikou (CN); Liming Zhang, Haikou (CN); Zhuoxuan Lv, Haikou (CN); Ying-Ying Lin, Haikou (CN); Jie Jiang, Haikou (CN)

(73) Assignee: Hainan Medical University, Haikou (CN)

( * ) Notice: Subject to any disclaimer, the term of this patent is extended or adjusted under 35 U.S.C. 154(b) by 0 days.

(21) Appl. No.: 16/842,730

(22) Filed: Apr. 7, 2020

(65) Prior Publication Data
US 2020/0330573 A1    Oct. 22, 2020

(30) Foreign Application Priority Data

Apr. 22, 2019 (CN) .......................... 201910322888.3

(51) Int. Cl.
| | | |
|---|---|---|
| *A61K 39/00* | (2006.01) | |
| *A61K 39/108* | (2006.01) | |
| *C12N 1/06* | (2006.01) | |
| *A61P 35/00* | (2006.01) | |

(52) U.S. Cl.
CPC ...... *A61K 39/0011* (2013.01); *A61K 39/0258* (2013.01); *A61P 35/00* (2018.01); *C12N 1/06* (2013.01); *A61K 2039/5152* (2013.01); *A61K 2039/521* (2013.01)

(58) Field of Classification Search
None
See application file for complete search history.

(56) References Cited

U.S. PATENT DOCUMENTS

| | | | |
|---|---|---|---|
| 2004/0101531 A1 | 5/2004 | Curtiss | |
| 2010/0216233 A1* | 8/2010 | Grillot-Courvalin | ....................... A61K 48/0008 435/325 |
| 2015/0064215 A1* | 3/2015 | Huang | .................. C12N 15/87 424/200.1 |
| 2020/0121773 A1* | 4/2020 | Stewart | .......... A61K 39/001154 |
| 2020/0330573 A1* | 10/2020 | Tan | .......................... C12N 1/20 |
| 2020/0345822 A1* | 11/2020 | Tan | .................... A61K 39/0011 |
| 2021/0361764 A1* | 11/2021 | Fotin-Mleczek | ...... A61K 39/39 |

FOREIGN PATENT DOCUMENTS

| | | | | |
|---|---|---|---|---|
| CN | 101010002 A | 8/2007 | | |
| CN | 107847577 A | 3/2018 | | |
| WO | WO-2004096270 A1 * | 11/2004 | ............. | A61K 39/39 |
| WO | WO-2015032165 A1 * | 3/2015 | ......... | A61K 48/0025 |
| WO | WO-2018078053 A1 * | 5/2018 | ............. | A61K 39/39 |

OTHER PUBLICATIONS

Dobrovolskienen et al. Vaccine, 2018. 36:4171-4180. available onlne: Jun. 9, 2018 (Year: 2018).*

* cited by examiner

*Primary Examiner* — Nita M. Minnifield

(57) ABSTRACT

Disclosed are a bacteriologically-modified whole-cell tumor vaccine and a method of making the same. The method includes: lysing bacteria at logarithmic growth phase to obtain a bacterial lysate; mixing the bacterial lysate with an excessive amino compound solution to aminate the bacterial lysate in the presence of EDC; mixing the aminated bacterial lysate with the tumor cells for a certain period of time to produce bacteriologically-modified tumor cells; and inactivating the bacteriologically-modified tumor cells to produce the bacteriologically-modified whole-cell tumor vaccine. The bacteriologically-modified whole-cell tumor vaccine has been demonstrated to have desirable therapeutic effect in tumor model mice.

7 Claims, 3 Drawing Sheets

BACTERIOLOGICALLY-MODIFIED WHOLE-CELL TUMOR VACCINE AND METHOD OF MAKING SAME

CROSS-REFERENCE TO RELATED APPLICATIONS

This application claims the benefit of priority from Chinese Patent Application No. 201910322888.3, filed on Apr. 22, 2019. The content of the aforementioned application, including any intervening amendments thereto, is incorporated herein by reference in its entirety.

TECHNICAL FIELD

This application relates to whole-cell tumor vaccines and preparation methods therefor, and more particularly to a novel whole-cell tumor vaccine having potential therapeutic effect on a tumor and a method of making the same.

BACKGROUND OF THE INVENTION

The recognition of the immune system for danger signals plays a key role in the immune responses. The danger signals are generally divided into two categories according to the sources, specifically, for exogenous pathogens, the danger signals are pathogen-associated molecular patterns (PAMPs), while for autogenous abnormal cells, the danger signals are damage-associated molecular patterns (DAMPs). Currently, almost all effective vaccines in use target pathogenic microorganisms such as bacteria and viruses, which is mainly because that bacteria and viruses have effective PAMPs which can be recognized by the immune system.

There are various immunotherapies available for tumors, which can be generally summarized into two categories: passive and active immunities. The passive immunity involves tumor-specific antibodies, cytokines and adoptive immunoreactive cells, while the active immunity includes tumor-specific or tumor-associated antigen protein or polypeptide vaccines, dendritic cell (DC) vaccines, allogeneic or heterogeneous whole-cell tumor vaccines and checkpoint blockers.

Whole-cell tumor vaccine is one of the tumor model vaccines for active immunotherapy of tumors. Since the tumor cells are autologous and have poor immunogenicity, and the immune system has an immune tolerance to the autologous tumor cells, it fails to achieve desired effect in the direct use of autologous tumor cells undergoing a treatment (such as irradiation) to lose the proliferative ability as a vaccine. Therefore, how to enable the immune system to recognize the autologous cell antigen to break the immune tolerance is crucial in the preparation of the whole-cell tumor vaccine. In 1993, Dranoff et al. from UK transferred granulocyte-macrophage colony-stimulating factor (GM-CSF) into melanoma cells for expression and then treated the melanoma cells with radiation for use as a whole-cell vaccine. It has been found in the melanoma model mice that the whole-cell vaccine can induce the migration, differentiation and maturation of dendritic cells (DCs) capable of processing tumor antigens in situ, inducing tumor-specific immune responses. From then on, the primary strategy to break through the immune tolerance for the whole-cell tumor vaccine is to modify the tumor cells through various methods. U.S. scientists have expressed NY-ESO-1 molecule in kidney cancer cells which can allow the innate immune system to interact with DCs, and then the NY-ESO-1 molecule is found to be able to promote the DCs to powerfully treat and present tumor antigens, inducing effective tumor-specific immune response. Researchers from Ireland use tumor-specific photothermal treatment to allow tumor tissues to release tumor antigens in situ and then employ a nano-material to accelerate the presentation to process tumor antigens, which can effectively induce the tumor-specific immune response. Moreover, some researchers from Chinese Academy of Sciences use a nano-biomaterial to transfer several immune-enhancing components (GM-CSF and IL-2) into tumor cells to produce a whole-cell tumor vaccine, which has a better anti-tumor effect than the single-component vaccine. Currently, though several whole-cell tumor vaccines have been developed and subjected to clinical trial, the therapeutic effect is not satisfactory after the trial enters stage III. Therefore, the existing whole-cell tumor vaccines are still required to be improved to be truly suitable for clinical applications.

SUMMARY OF THE INVENTION

An object of this application is to provide a bacteriologically-modified whole-cell tumor vaccine and a method of making the same, where the vaccine is mainly characterized by the layer of bacterial antigens coated on the surface of the tumor cells. The process of coating bacterial antigens on the surface of tumor cells is referred to as bacteriological modification, and the bacteriologically-modified tumor cells are inactivated to produce the tumor-specific vaccine. The tumor model mice, after vaccinated subcutaneously, intravascularly, intramuscularly or intraperitoneally with the bacteriologically-modified tumor cells, are induced to generate a specific immune response, which indicates that the bacteriologically-modified whole-cell tumor vaccine has a desired therapeutic effect on tumors, having a good application prospect.

In the invention, the process of adhesively coating the typical pathogenic bacterial lysate mainly containing proteins as antigens on the surface of the tumor cells is referred to as the bacteriological modification of tumor cells, which is intended to artificially introduce bacterial PAMPs to the tumor cells. Bacterial lysate is mixed with excess amino compounds (such as ethylenediamine) under neutral or weakly alkaline conditions. 1-ethyl-(3-dimethylaminopropyl) carbodiimide (EDC) is then introduced, and the amino group of the amino compound is condensed with the carboxyl group of the protein of the bacterial lysate, so that the bacterial lysate is aminated and positively charged in a physiological environment. Specifically, the carboxyl group on the bacterial protein is reacted with one amino group of ethylenediamine to form an amide bond in the presence of EDC, rendering the aminated protein positively charged in a physiological solution. Thereafter, the aminated protein is bound to the surface of the tumor cells through electrostatic attraction to produce the bacteriologically-modified tumor cells, which are inactivated and then used as a whole-cell tumor vaccine. It has been observed herein that the vaccination of the bacteriologically-modified tumor cells could effectively induce a tumor-specific immune response in tumor model mice, having a good therapeutic effect on tumors. The invention provides a method of preparing a whole-cell tumor vaccine through the bacteriological modification of tumor cells, which is a new strategy for preparing a whole-cell tumor vaccine and has a brilliant clinical application prospect.

The technical solutions of the invention are described as follows.

The invention provides a method of preparing a bacteriologically-modified whole-cell tumor vaccine, comprising:

(1) mixing an amino compound at an excessive amount with a bacterial lysate under neutral or weakly alkaline conditions to allow an amino group to react with the carboxyl group of a protein of the bacterial lysate to aminate the bacterial lysate;

(2) mixing the aminated bacterial lysate prepared in step (1) with tumor cells under gentle shaking to allow the aminated bacterial lysate to be bound to a surface of the tumor cells through electrostatic attraction to produce bacteriologically-modified tumor cells; and (3) inactivating the bacteriologically-modified tumor cells to produce the bacteriologically-modified whole-cell tumor vaccine.

In an embodiment, the step (1) comprises:

(1-1) culturing bacteria; collecting the bacteria followed by freezing-thawing and ultrasonication to produce a supernatant as the bacterial lysate; and lyophilizing the bacterial lysate;

(1-2) mixing the amino compound at an excessive amount with the lyophilized bacterial lysate in ultrapure water; wherein the amino compound is selected from the group consisting of ethylenediamine, N,N-dimethylethylenediamine, polyethyleneimine and a combination thereof;

(1-3) adding 1-ethyl-(3-dimethylaminopropyl) carbodiimide (EDC) to the reaction mixture; and stirring the reaction mixture at 4° C. with the new EDC added at an interval;

(1-4) dialyzing the reaction mixture in ultrapure water to remove the free amino compound and EDC to produce a solution of the aminated bacterial lysate; and (1-5) adjusting the solution of the aminated bacterial lysate to pH 7-9.

In an embodiment, the amino compound is ethylenediamine; and in step (1-3), the stirring is performed for 48-52 h.

In an embodiment, the bacterial lysate is prepared through the steps of:

culturing bacteria to a logarithmic growth phase; and harvesting the bacteria;

freezing the bacterial in liquid nitrogen at −160° C. for more than half an hour and thawing the frozen bacterial completely in a water bath at 37° C.; and repeating the freezing and thawing three times;

rupturing the thawed bacterial under ultrasonication followed by centrifugation at 10,000 rpm and 4° C. for 10-12 min to collect a supernatant as the bacterial lysate; and freezing the bacterial lysate at −80° C. followed by lyophilization to produce bacterial lysate powder.

In an embodiment, the step (1) comprises:

dissolving 10 mg of the bacterial lysate powder completely with 1 mL of ultrapure water at 4° C. to produce a first solution; mixing 10 µL of ethylenediamine having a purity of 99.5% or more with 0.5 mL of ultrapure water uniformly at 4° C. followed by adjustment to pH 7-9 and adding with ultrapure water to 1 mL at 4° C. to produce a second solution; dissolving 5 mg of EDC with 125 µL of ultrapure water at 4° C. to produce a third solution;

stirring the first solution gently in a flask using a magnetic stirrer;

adding the second solution to the first solution slowly; mixing the reaction mixture completely; adding the third solution to the reaction mixture slowly; stirring the reaction mixture at 4° C. for 48 h, wherein the third solution is additionally added respectively at the $16^{th}$ and $32^{nd}$ h of the stirring to enable the EDC to persistently work;

loading the reaction mixture in a dialysis bag (14K MWCO); dialyzing the reaction mixture in 1 L of ultrapure water at 4° C. for 48 h to produce a solution of the aminated bacterial lysate, wherein the ultrapure water is replaced every other 8-12 h; and adjusting the solution of the aminated bacterial lysate with a 12 mol/L hydrochloric acid solution or a 1 mol/L sodium hydroxide solution to pH 7-9;

wherein the solution of the aminated bacterial lysate is determined using a BCA kit for protein content and then adjusted with PBS to a protein content of 0.2 mg/100 µL.

In an embodiment, the bacteria are selected from the group consisting of *E. coli*, *Mycobacterium tuberculosis*, *Staphylococcus*, *Pseudomonas* and *Klebsiella pneumonia*.

In an embodiment, culturing the tumor cells in vitro to logarithmic growth phase; harvesting and counting the tumor cells; adjusting the tumor cells with PBS to produce a tumor cell suspension having a content of $1 \times 10^6$ cells/100 µL;

mixing 50 µL of the tumor cell suspension with 50 µL of the solution of the aminated bacterial lysate uniformly; and shaking the reaction mixture gently at room temperature for 30-50 min, preferably 30 min, to produce the bacteriologically-modified tumor cells.

In an embodiment, the inactivation is performed using an X-ray irradiator at an irradiation intensity of 80-100 Gy. The inactivation is intended to enable the bacteriologically-modified tumor cells, after injected as a vaccine, to fail to grow, proliferate and metastasize any longer, ensuring the safe use of the vaccine.

In an embodiment, individual mice are vaccinated subcutaneously, intramuscularly, intravascularly or intraperitoneally with $3-5 \times 10^5$ bacteriologically-modified tumor cells. The bacteriologically-modified whole-cell tumor vaccine can induce a tumor-specific immune response in the tumor model mice, which indicates a good therapeutic effect on tumors, having a brilliant application prospect in the treatment of human tumors.

Further, the invention also provides a bacteriologically-modified whole-cell tumor vaccine prepared using the above method.

Compared to the prior art, the invention has the following beneficial effect.

The invention provides a bacteriologically-modified whole-cell tumor vaccine and a method of making the same. In the method, a layer of bacterial antigens is coated on the surface of the tumor cells (this process is referred to as bacteriological modification) to produce bacteriologically-modified tumor cells, which are then inactivated to prepare the tumor-specific vaccine. Through the bacteriological modification, the tumor cells are artificially provided with bacterial PAMPs.

The bacteriologically-modified tumor cells, after injected as a vaccine to tumor model mice, are found to be capable of inducing a tumor-specific immune response, having a good therapeutic effect on tumors. The method provided herein for preparing a whole-cell tumor vaccine through the bacteriological modification of tumor cells is a new preparation strategy of a whole-cell tumor vaccine and has a brilliant clinical application prospect. In the actual application, tumor cells isolated from tumor tissues of a patient with a tumor are employed to prepare the tumor-specific bacteriologically-modified vaccine. The invention provides feasibility and technical support for the treatment on human tumors.

DETAILED DESCRIPTION OF EMBODIMENTS

The invention will be further described below with reference to the embodiments, but these embodiments are not intended to limit the invention. Various modifications and changes made based on the content disclosed herein should fall within the scope of the invention.

Figure 1:
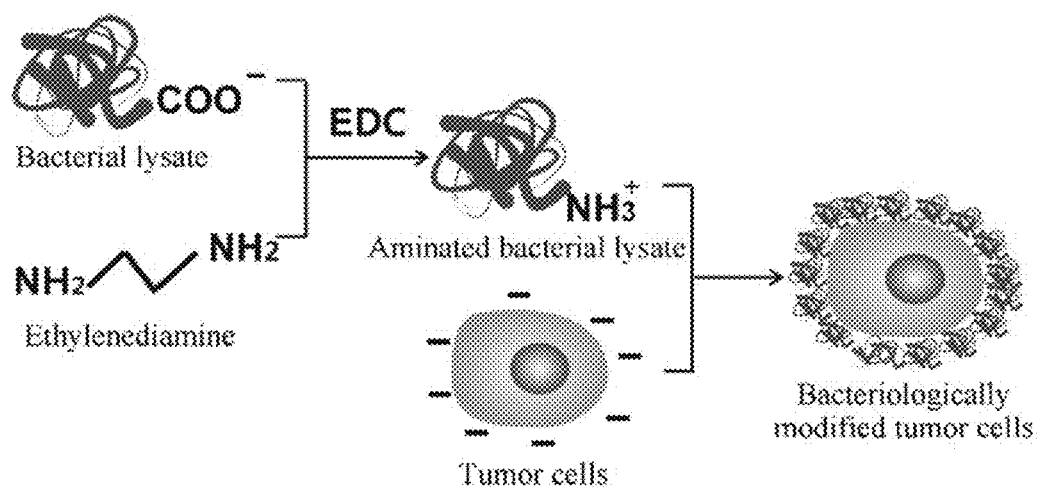
FIG. 1 schematically shows the preparation of bacteriologically-modified tumor cells of the invention.

FIG. 1 schematically shows the preparation of bacteriologically-modified tumor cells of the invention, specifically, an excessive positively-charged amino compound (such as ethylenediamine) is mixed with a bacterial lysate in the presence of EDC to allow the amino compound to react with the protein of the bacterial lysate to render the bacterial lysate positively-charged. Then the bacterial lysate is bound to the tumor cells through electrostatic attraction to produce the bacteriologically-modified tumor cells, which are inactivated to be used as the tumor vaccine.

1. Preparation of Bacterial Lysate (1) Preparation of bacteria medium (*E. coli*)

A liquid LB medium was specifically prepared as follows. 5 g of yeast extract, 10 g of tryptone and 10 g of NaCl were added to a vessel, to which 900 mL of deionized water was added. The mixture was adjusted to pH 7.2-7.4 with 1 mol/L NaOH, added with deionized water to 1 L and sterilized at 121° C. and 0.1-0.15 MPa for 20 min. For a solid LB medium, 15 g of agar was additionally added and the mixture was sterilized under high pressure and poured into special petri dishes for use.

(2) Culturing and Harvesting of Bacteria (*E. coli* JM 109)

*E. coli* JM 109 stored in glycerol at −80° C. was transferred to a 0° C. ice bath, and a small amount of frozen bacterial solution was picked up with a disinfected toothpick or an inoculation loop to be uniformly dispersed onto the solid LB medium. Then the medium was cultured at 37° C. in an incubator for 8-12 h to allow the single colony to appear. On the next day, a single colony was picked with a disinfected toothpick or an inoculation loop and added to 30 mL of liquid LB medium. The liquid medium was cultured in a shaker at 37° C. and 225 rpm for 12-16 h. Then the bacterial suspension was added to fresh liquid LB medium in a volume ratio of 1:100, and the fresh medium was cultured in a shaker at 37° C. and 225 rpm to an OD value of 0.5-0.6 (cultured for about 2.5 h) and centrifuged at 4° C. and 5000×g for 5 min. The supernatant was discarded and the bacterial cells were collected.

(3) Preparation of *E. coli* Lysate

The bacterial cells obtained above were washed twice with PBS pre-cooled at 4° C. for more than 5 h and then washed once with ultrapure water at 4° C. The cells were resuspended with ultrapure water having a volume 1/10 of the original medium at 4° C., frozen at −160° C. in liquid nitrogen for more than half an hour and thawed completely in a 37° C. water bath. The process of freezing and thawing was repeated three times, and the thawed cells were ruptured by ultrasonication. During the ultrasonication, the container containing the bacterial suspension was placed in cool water (4° C.) and the probe should be placed 1/3 below the liquid surface. The ultrasonication was performed intermittently at a power of 30%, specifically, the probe was operated for 3 s and then stopped for 5 s. The ultrasonication was performed three times each for 10 min, and there was an interval of 10 min between adjacent two ultrasonic treatments. Then the bacterial suspension was centrifuged at 4° C. and 10,000 rpm for 10 min to collect a supernatant as a bacterial lysate. The bacterial lysate was immediately frozen at −80° C. and lyophilized using a lyophilizer (Labconco FreeZonc®4.5 Freeze Dryer). The lyophilized lysate was stored at −20° C. for use.

2. Amination of Bacterial Lysate (1) Preparation of Solutions 10 mg of the lyophilized lysate was dissolved completely in 1 mL of ultrapure water at 4° C. to produce a first solution. 10 µL of ethylenediamine (purity >99.5%) was mixed uniformly with 0.5 mL of ultrapure water at 4° C., adjusted to pH 8-9 with hydrochloric acid (12 mol/L) or sodium hydroxide (1 mol/L) and added with ultrapure water at 4° C. to 1 mL to produce a second solution. 5 mg of EDC was dissolved in 125 µL of ultrapure water at 4° C. to produce a third solution. The above solutions were prepared based on 10 mg of the lyophilized lysate, and can be accordingly adjusted according to the amount of lyophilized lysate.

(2) Amination of Bacterial Lysate

The first solution was added to a flask and slightly stirred using a magnetic stirrer (set to 2-3 level, about 200-400 rpm). Then the second solution was slowly added to the first solution. After the first solution and the second solution were completely mixed, the third solution was slowly added, and the reaction mixture was stirred at 4° C. for 48 h to produce an aminated bacterial lysate, where the third solution was additionally added every other 8-12 h, each for 125 µL, to enable the EDC to persistently work.

(3) Preparation of a Solution of the Aminated Bacterial Lysate

The aminated bacterial lysate was loaded in a dialysis bag (14K MWCO), and then dialyzed in 1 L of ultrapure water at 4° C. for 48 h to produce a solution of the aminated bacterial lysate, where the ultrapure water was replaced every other 8-12 h. The solution of the aminated bacterial lysate was adjusted to pH 8-9 with hydrochloric acid (12 mol/L) or sodium hydroxide (1 mol/L), where the solution of the aminated bacterial lysate was determined using a BCA kit for protein content and then adjusted with PBS to a protein content of 0.2 mg/100 µL.

3. Culturing and Harvesting of Tumor Cells

Tumor cells were transferred from a liquid nitrogen tank immediately to a 37° C. water bath and shaken repeatedly for complete dispersion (about 1-2 min). The cell solution was centrifuged at 2,000 rpm for 5 min, and the supernatant was removed. The cells were added with a corresponding medium (such as DMEM and RPMI 1640), fetal bovine serum, antibiotics and growth factors (referring to the instruction of the tumor cells for details), mixed uniformly and added to a tissue culture flask. The tissue culture flask was cultured at 37° C. and 5% $CO_2$, where the medium was replaced every other 1-2 days. When proliferating to occupy 80% of the space inside the culture flask, the cells were washed twice with PBS, digested with 0.25% trypsin and continuously cultured in another culture flask. After proliferating to the desired number, the cells were washed with PBS twice again, digested with 0.25% trypsin and centrifuged at 2,000 rpm for 5 min. The supernatant was discarded, and the cells were washed twice with PBS and counted. The tumor cells were adjusted to a content of $1\times10^6$ cells/100 μL with PBS for subsequent use.

Figure 2A:
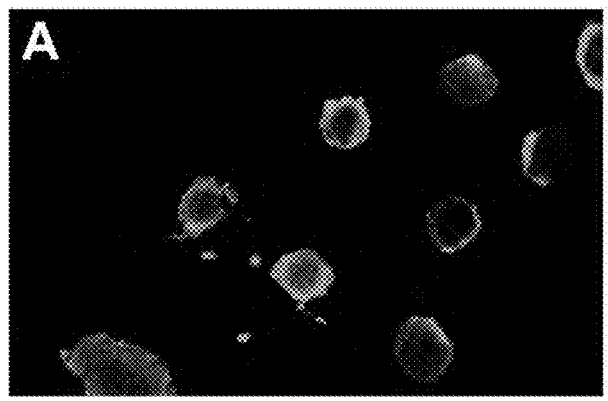
FIG. 2A is a confocal micrograph showing the FITC-labeled aminated bacterial lysate (green fluorescence)
Figure 2B:
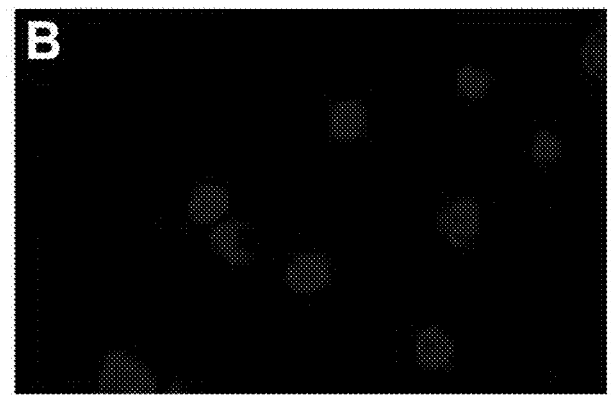
FIG. 2B is a confocal micrograph showing the tumor cells bacteriologically-modified with the FITC-labeled aminated bacterial lysate with nuclei further stained with DAPI (blue fluorescence); where FIG. 2A and FIG. 2B share the same vision field.
Figure 2C:
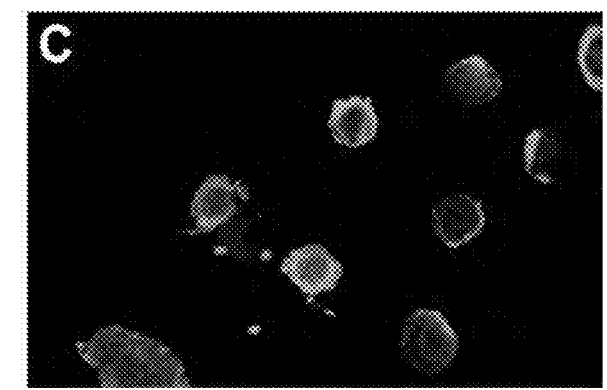
FIG. 2C shows the superimposition of FIGS. 2A and 2B.

4. Preparation of Bacteriologically-Modified Whole-Cell Tumor Vaccine (1) Bacteriological modification of tumor cells 50 μL of the above tumor cell suspension (containing $0.5\times10^6$ cells) and 50 μL of the solution of the aminated bacterial lysate (containing 0.1 mg of protein) were mixed uniformly and shaken gently at room temperature for 30 min to produce the bacteriologically-modified tumor cells (FIGS. 2A-2C). FIGS. 2A-2C show the primary features of the bacteriologically-modified tumor cells of the invention observed under a confocal microscope, where FIG. 2A shows the FITC-labeled aminated bacterial lysate (green fluorescence); FIG. 2B shows tumor cells bacteriologically-modified with the FITC-labeled aminated bacterial lysate with nuclei further stained with DAPI (blue fluorescence); FIG. 2A and FIG. 2B shares the same vision field; and FIG. 2C is the superimposition of FIGS. 2A and 2B and shows the relationship between the bacterial lysate (green fluorescence) and the nuclei (blue fluorescence). It can be confirmed by the figures that the aminated bacterial lysate was effectively bound to the surface of the tumor cells.

(2) Inactivation of Bacteriologically-Modified Tumor Cells

The above prepared bacteriologically-modified tumor cells were inactivated using an X-ray instrument (Rad Source RS2000 X-ray irradiator) at an irradiation intensity of 80-100 Gy to prepare the vaccine. Individual tumor model mice were vaccinated with $3\times10^5$-$5\times10^5$ cells subcutaneously, intravascularly, intramuscularly or intraperitoneally.

Figure 3A:
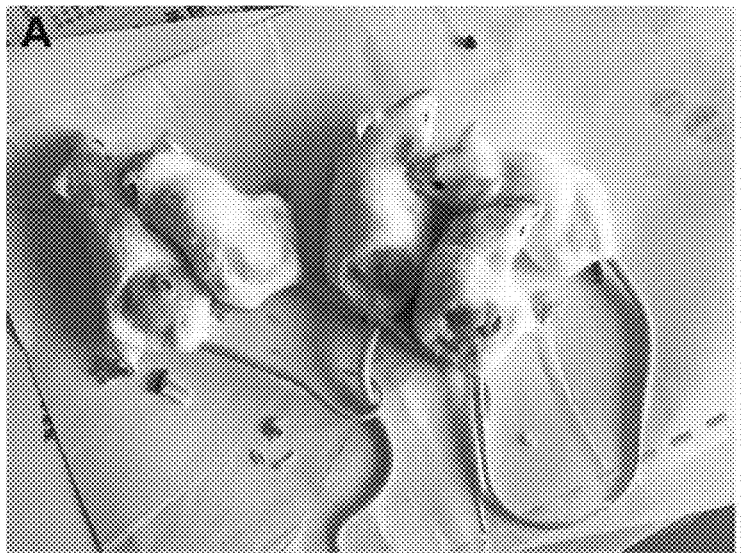
FIG. 3A shows mice in the group vaccinated with the bacteriologically-modified tumor cells according to an embodiment of the invention, where tumors of 3 of the 5 mice from the treatment group completely or almost completely disappear, and the other two mice have a tumor significantly smaller in size than the mice in the control.
Figure 3B:
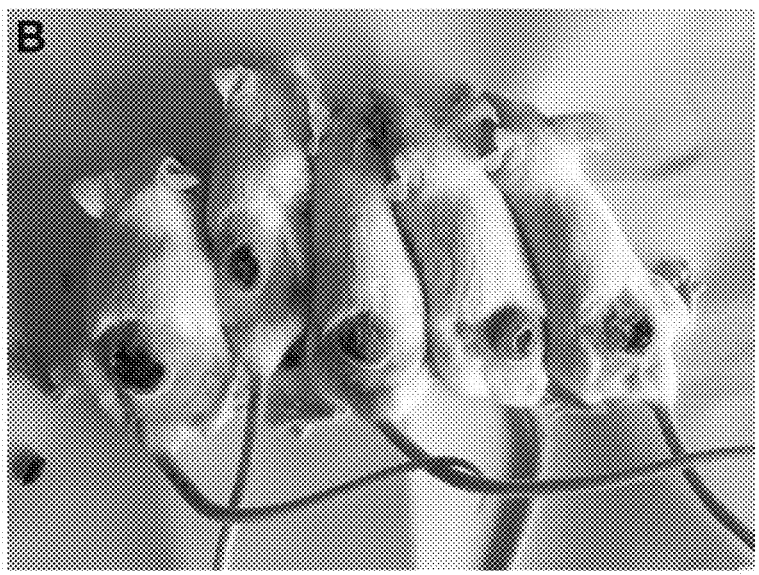
FIG. 3B shows the control group in which the mice were not treated.

5. Verification of Therapeutic Effect 10 female BALB/c mice, aged 6-8 weeks, were selected and averagely divided into two groups, i.e., treatment group and control group. The 10 mice were respectively injected subcutaneously with $2\times10^6$ murine CT26 colon cancer cells at the lower left side of the back to establish a tumor model. 5 mice in the treatment group were further injected subcutaneously with $5\times10^5$ of the inactivated bacteriologically-modified CT26 colon cancer cells (dissolved in 100 μL of PBS) at the upper right side of the back. The tumor growth in mice was monitored, and the mice were sacrificed 28 days after injection of tumor cells. The serum was collected and detected for the specific antibodies against the CT26 colon cancer cells, and the spleen lymphocytes were used as effector cells in the killing experiments of the CT26 colon cancer cells. It can be seen from the results that the tumor disappeared completely or almost completely in 3 of the 5 mice in the treatment group and the tumors in the other two mice were significantly smaller than those in the mice of the control group (as shown in FIGS. 3A-3B). Moreover, with regard to the mice from the treatment group, specific antibodies against the CT26 colon cancer cells were found in the serum thereof, and their lymphocytes had significant killing effect on the CT26 colon cancer cells. These experimental results demonstrated that the bacteriologically-modified CT26 whole-cell tumor vaccine can effectively induce the immune response specifically against the CT26 colon cancer cells, effectively treating the murine colon cancer.

Described above are merely preferred embodiments of the invention, and these embodiments are not intended to limit the invention. Various modifications, changes and replacements made based on the content of the invention should fall within the scope of the invention.

What is claimed is:

1. A method of preparing a bacteriologically-modified whole-cell tumor vaccine, comprising:
   (1) mixing an amino compound with a bacterial lysate under neutral or weakly alkaline conditions to allow an amino group positively charged in the amino compound to react with a carboxyl group of a protein of the bacterial lysate to aminate the bacterial lysate;
   (2) mixing the aminated bacterial lysate prepared in step (1) with tumor cells under gentle shaking to allow the aminated bacterial lysate to be bound to a surface of the tumor cells through electrostatic attraction to produce bacteriologically-modified tumor cells; and
   (3) inactivating the bacteriologically-modified tumor cells to produce the bacteriologically-modified whole-cell tumor vaccine.

2. The method of claim 1, wherein a solution of the aminated bacterial lysate is prepared through steps of:
   (1-1) culturing bacteria; collecting the bacteria followed by freezing-thawing and ultrasonication to produce a supernatant as the bacterial lysate; and lyophilizing the bacterial lysate;
   (1-2) mixing the amino compound with the lyophilized bacterial lysate in ultrapure water; wherein the amino compound is selected from the group consisting of ethylenediamine, N,N-dimethylethylenediamine, polyethyleneimine and a combination thereof;
   (1-3) adding 1-ethyl-(3-dimethylaminopropyl) carbodiimide (EDC) to the reaction mixture; and stirring the reaction mixture at 4° C. with fresh EDC added at an interval;
   (1-4) dialyzing the reaction mixture in ultrapure water to remove the free amino compound and EDC to produce a solution of the aminated bacterial lysate; and
   (1-5) adjusting the solution of the aminated bacterial lysate to pH 7-9.

3. The method of claim 2, wherein the amino compound is ethylenediamine; and in step (1-3), the stirring is performed for 48-52 h.

4. The method of claim 1, wherein the bacterial lysate is prepared through steps of:
   culturing bacteria to a logarithmic growth phase; and harvesting the bacteria;
   freezing the bacteria in liquid nitrogen at −160° C. for more than half an hour and thawing the frozen bacterium completely in a water bath at 37° C.; and repeating the freezing and thawing three times;
   rupturing the thawed bacteria under ultrasonication followed by centrifugation at 10,000 rpm and 4° C. for 10-12 min to collect a supernatant as the bacterial lysate; and
   freezing the bacterial lysate at −80° C. followed by lyophilization to produce bacterial lysate powder.

5. The method of claim 1, wherein the bacteriologically-modified tumor cells are prepared through steps of:
   culturing the tumor cells in vitro to logarithmic growth phase; harvesting and counting the tumor cells; adjusting the tumor cells with PBS to produce a tumor cell suspension having a content of $1\times10^6$ cells/100 μL; and mixing 50 μL of the tumor cell suspension with 50 μL of the solution of the aminated bacterial lysate uniformly; and shaking the reaction mixture gently at room temperature for 30 min to produce the bacteriologically-modified tumor cells.

6. The method of claim 1, wherein the bacterial lysate is derived from bacteria selected from the group consisting of *E. coli, Mycobacterium tuberculosis, Staphylococcus, Pseudomonas* and *Klebsiella pneumoniae*.

7. The method of claim 1, wherein the inactivation is performed using an X-ray irradiator at an irradiation intensity of 80-100 Gy.

* * * * *